United States Patent
Rajan

[11] Patent Number: 5,980,461
[45] Date of Patent: Nov. 9, 1999

[54] ULTRASOUND IMAGING APPARATUS FOR MEDICAL DIAGNOSTICS

[76] Inventor: Subramaniam D. Rajan, 5907 106th Ave. NE., Kirkland, Wash. 98033

[21] Appl. No.: 09/071,648

[22] Filed: May 1, 1998

[51] Int. Cl.[6] ........................................ A61B 8/00
[52] U.S. Cl. ............................................. 600/459
[58] Field of Search ...................... 600/447, 459, 600/472; 128/916

[56] References Cited

U.S. PATENT DOCUMENTS

| | | |
|---|---|---|
| 4,246,791 | 1/1981 | Glenn . |
| 4,275,597 | 6/1981 | Quedens et al. . |
| 4,281,550 | 8/1981 | Erickson . |
| 4,391,281 | 7/1983 | Green . |
| 4,570,488 | 2/1986 | Miwa et al. . |
| 4,594,662 | 6/1986 | Devaney . |
| 5,042,492 | 8/1991 | Dubut ........................................ 600/459 |
| 5,282,471 | 2/1994 | Sato ........................................... 128/916 |
| 5,370,120 | 12/1994 | Oppelt et al. ............................. 128/916 |
| 5,503,152 | 4/1996 | Oakley et al. . |
| 5,645,066 | 7/1997 | Gandini et al. .......................... 128/916 |

*Primary Examiner*—Brian L. Casler
*Assistant Examiner*—Maulin Patel
*Attorney, Agent, or Firm*—Paul Griffiths

[57] ABSTRACT

A hand held ultrasound system is disclosed. By use of a curved reflector for focusing sound energy reflected by a structure being imaged a simple, lightweight, and power efficient device is presented. A transmitter directs a sound wave into a patients body, a structure to be imaged reflects some of the sound wave, a curved reflector focuses that sound energy onto one or more receivers. If more than one receiver is used they do not need to be phased since this function is performed by the curved reflector. The reflector may be spherically shaped or ellipsoidal. The device can function in either mono-static mode or bi-static mode depending on the depth of focus required, e.g., for imaging structures close to the skin surface (blood vessels and the like) an ellipsoidal shaped reflector is used since it provides a very short or close-up depth of focus. The device provides good resolution while using relatively little power making the device light in weight and small in size.

7 Claims, 3 Drawing Sheets

ULTRASOUND IMAGING APPARATUS FOR MEDICAL DIAGNOSTICS

BACKGROUND OF THE INVENTION

1. Technical field

The present invention relates to ultrasound imaging devices for medical diagnostics and in particular to a hand held apparatus for producing two-dimensional and three-dimensional images of structures within a patient's body such as organs and blood vessels.

2. Background Information

It is well know to use sound waves in the two to ten megahertz range for producing images of internal structures, especially of a medical patient's organs. A device transmits a sound wave, receives, and processes reflected sound wave energy to produce an image. Such devices may use one transducer or a plurality of transducers arranged in an array. A transducer can either transmit a signal, receive a signal, or perform both tasks. As sound waves produced by one or more transducers travel through soft tissue some of the sound waves are reflected back toward the source. A receiver(s) senses this sound energy and creates a signal that can be electronically translated into a viewable image, usually on a monitor.

Devices of this type for use in the medical field are generally referred to as ultrasound systems. Modern ultrasound systems generally use a plurality of transducers arranged in a linear or circular array. By suitably adjusting the phase on each transducer, sound energy is focused on a small region of an object being imaged. This focusing procedure is generally referred to as beam forming. In the receive mode, transducers can also be phased to receive energy from a selected region within the object being imaged. By repeating this process a high resolution image of the object is obtained by adding all of the individual images together.

Since ultrasound systems are so useful as a diagnostic tool, there is a great need to provide a simple to use and relatively inexpensive device for imaging internal human structures. The device needs to be small enough to be hand held and have reasonably small power requirements. This type of device would be invaluable in a clinic or doctor's office setting where larger and/or more expensive devices are not feasible. The bulk, weight and size of ultrasound systems results from the amount of electronics needed to perform beam-forming operations. Developmental efforts are being directed at the design of specialized micro-chips to perform the beam forming operations. It is hoped that incorporation of these micro-chips will reduce the over all weight and size of the systems.

An alternative approach is to avoid the use of an array by using a single transducer that acts as both a transmitter and receiver, referred to as mono-static. These transducers are shaped to focus sound. In order to image an object, the transducer is rotated mechanically by a stepper motor or the like. The echo signals are arranged to give an image of the object. The disadvantages of this approach are the limitations on resolution imposed by the depth of focus of the transducer and the scanning rate, and the power requirements for a mechanical sector scanner. These devices only produce two-dimensional images. The present invention solves these problems by improving the image quality, or resolution, and by using less power, thereby prolonging battery life which reduces the cost of the device.

It is also known to use a two-dimensional receiver matrix to produce a three-dimensional image. A limiting factor on the design of systems for three-dimensional imaging is the required resolution of the resulting images. Current systems use a phased array scheme to form a scan beam and to receive the signal reflected by the structures to be imaged. Three-dimensional systems currently use planar arrays. Systems can vary by the number of elements in an array and are directly related to the image resolution. In a system having an array of 64×64 elements the total number of elements is 4,096. The electronics associated with the phasing of this number of elements requires increased size, weight, and cost of the system. The medical field would greatly benefit from a device that alleviates the foregoing problems. The currently available hand held systems do not provide three-dimensional imaging.

The present invention does not require any mechanical scanning or the electronics for beam-forming operations. The scan beams are formed simultaneously through the use of a curved reflector, thereby reducing the time required to produce an image. This also reduces the power consumption of the unit, which in turn reduces the size and weight of a battery pack. The scan beams of the present invention can be focused both in a transmit mode and receive mode by selection of a suitably shaped acoustic reflector (lens). This provides increased resolution without penalty of greater size or weight. By utilizing a two-dimensional array of signal receivers a three-dimensional image is possible. Scan beam forming of the present invention is done with inexpensive components compared to phased array systems making it a breakthrough development in three-dimensional imaging and hand-held devices.

SUMMARY OF THE INVENTION

A hand held ultrasound imaging apparatus for medical diagnostics is disclosed. The apparatus includes a signal transmitter, or transducer, to generate a signal in the two to ten megahertz range. The transmitters are held in position by suitable means. The transmitter emits sound energy in beam form toward the structure to be imaged. A broad beam is used to encompass a wide area. Reflected acoustic energy propagates back toward the signal reflector.

An array of receivers is held at the focal plane with the receivers facing the reflector. The signal reflector collects and focuses a return signal onto the array of receivers. In this manner different receivers receive sound energy from a different direction thereby providing data encompassing a three dimensional volume. In this manner each receiver senses sound energy coming from a different location without resorting) to the use of phasing of the array elements or mechanical scanning. The raw data received by the receivers is amplified and feed into a scan converter for display on an appropriate monitor. The signal reflector, transmitter, and receivers are provided in an appropriate enclosure with the associated electronic circuits held in either the same enclosure or in their own, along with a battery pack, all connected by appropriate wire connections.

The instrument can be designed in a bi-static or mono-static mode. In the bi-static mode, the transmitter is separate from the receiver elements. In this mode the transmitter has either a single or a plurality of elements with sufficient beam width directed towards the object being imaged. In the mono-static configuration, the array of transducers function both as transmitters and receivers. In the transmit mode the sound waves from the transducers interact with the reflector producing a number of beams (equal to the umber of elements) each looking in different directions. The echo energy from the object is focused onto the transducers which now act as receivers and convert the sound energy into an electrical signal. This data is used to create an image of the object being scanned.

The signal reflector can be spherical in shape for imaging structures deeper with a human body while an ellipsoidal reflector can be used to improve image quality of structures nearer the skin, such as blood vessels. The reflectors are shaded to improve image quality.

Other features, objects and advantages of the invention are hereinafter described in the description of the best mode or preferred embodiment of the invention.

BRIEF DESCRIPTION OF THE DRAWING

In the drawings, like reference characters designate like parts throughout the several views, and.

DESCRIPTION OF THE PREFERRED EMBODIMENTS

Figure 1:
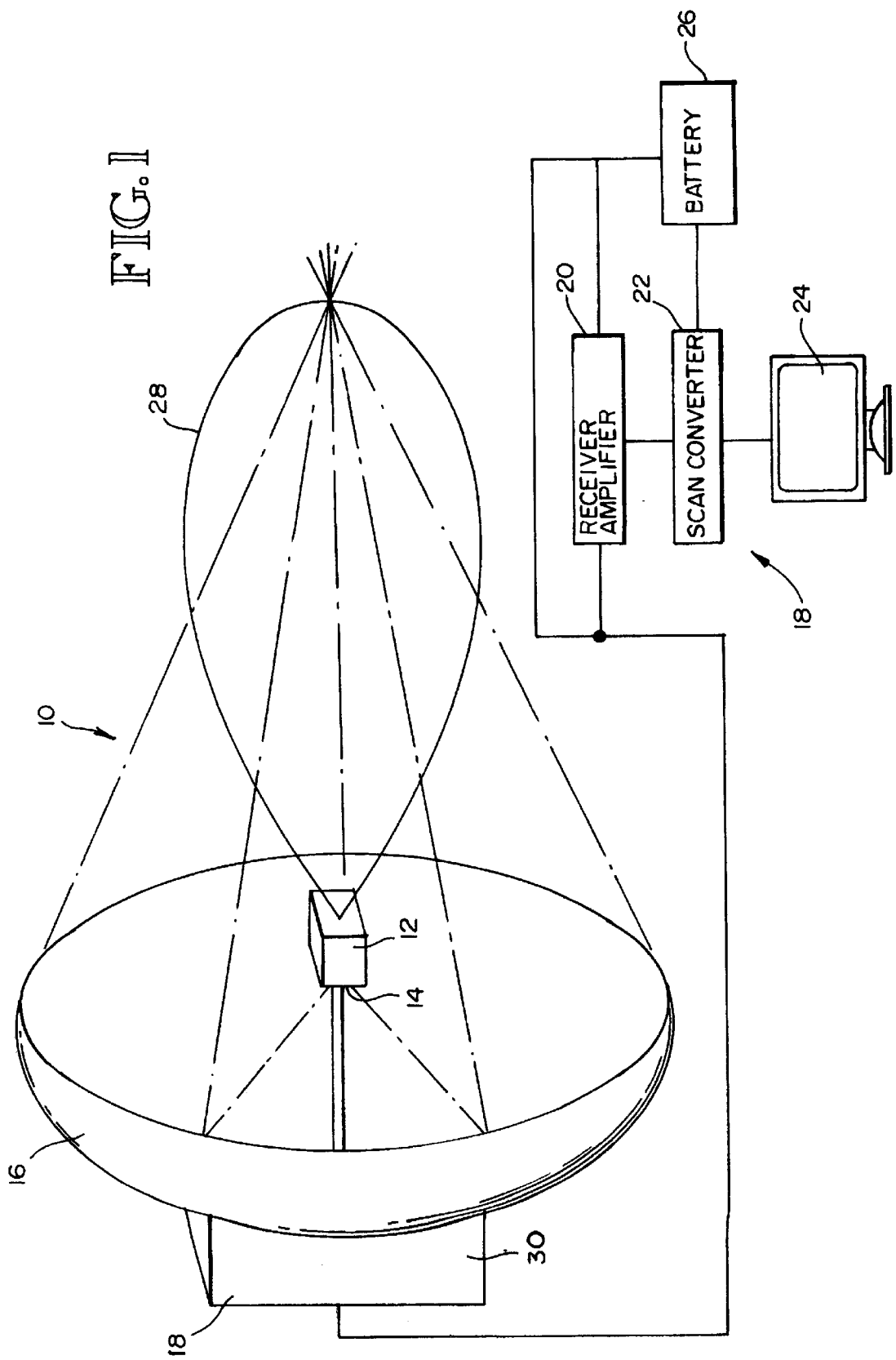
FIG. 1 is a view of a signal reflector, signal transmitter, and signal receivers, showing an approximation of a beam of energy generated, with electronics shown in schematic fashion.

Referring now to the several figures of the drawing, and first to FIG. 1, basic elements of a hand held ultrasound device operating in a bi-static mode are shown in schematic fashion. A scan head 10 includes a signal transmitter 12, an array of receivers 14, a signal reflector 16, and signal processing circuits 18. A receiver amplifier 20 and scan converter 22 may be packaged with a video monitor 24 of appropriate size. A battery pack 26 is provided as a power supply.

Figure 3:
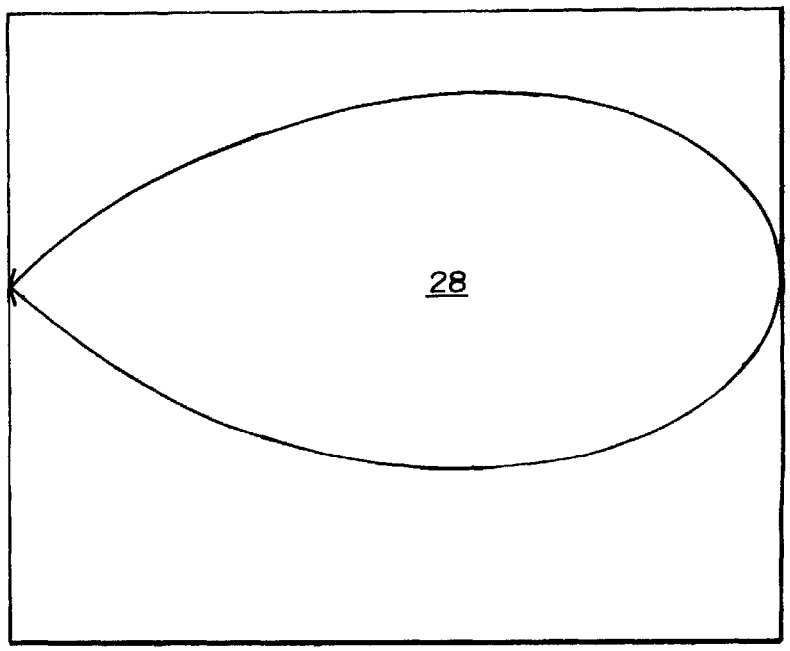
FIG. 3 is an approximation of a sound energy beam created using a beam angle of twenty five degrees.

Transmitter 12 may be any appropriate sound energy transmitter providing a pulsed scan beam in the range of two to ten megahertz. Preferably, signal transmitter 12 will be a piezoelectric ceramic element providing a scan beam 28 of twenty-five degrees as shown in FIGS. 1 and 3. This allows scan beam 28 to illuminate a wide area. A signal generator 30 is located in a base portion of scan head 10 thereby being located relatively close to transmitter 12.

Receiver array 14 is made up of a plurality of receivers arranged on a flat plane. Receiver array 14 is located at a focal plane of signal reflector 16. Receiver array 14 and signal transmitter 12 are held in position by a support rod 32. Support rod 32 also contains wire connections to and from receiver array 14 and signal transmitter 12. Scan head 10 includes a conventional electrical connection with display system electronics and power supply.

Figure 2:
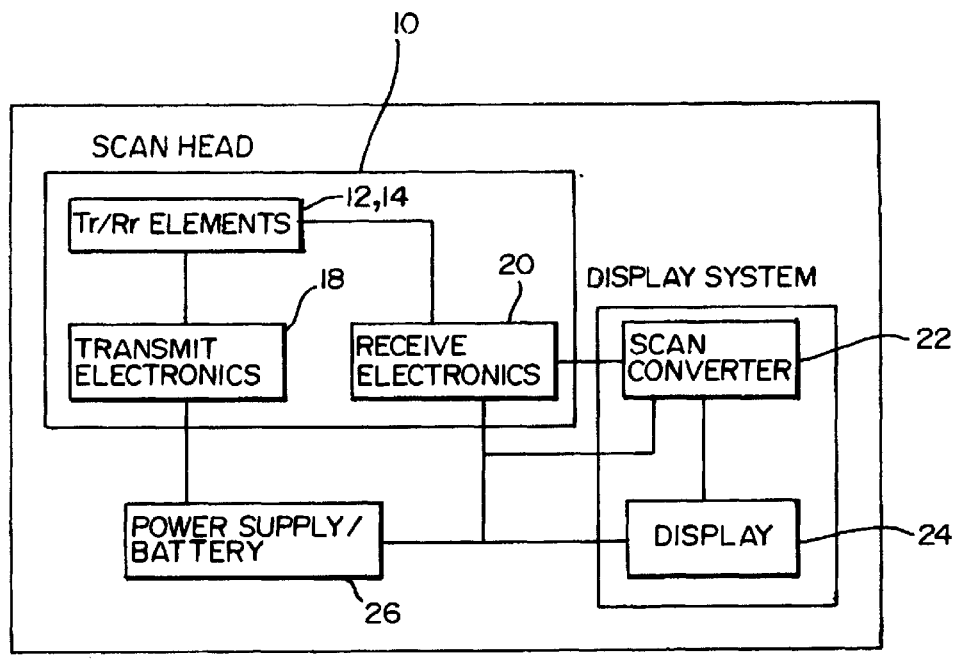
FIG. 2 is a schematic showing the relationship of the associated electronic and power supply.

Referring now to FIG. 2, a schematic of the associated electronics is illustrated. As mentioned above signal transducer electronics 18 and signal receiver electronics 20 are contained with scan head 10 since they must be located as close as possible to signal transmitter 12 and receiver array 14 to reduce or prevent cross talk. Located in a separate unit are power supply 26 and scan converter electronics 22 along with a display 24. Power supply 26 can be by way of fixed power lead from an outside source or by a battery pack.

Figure 4:
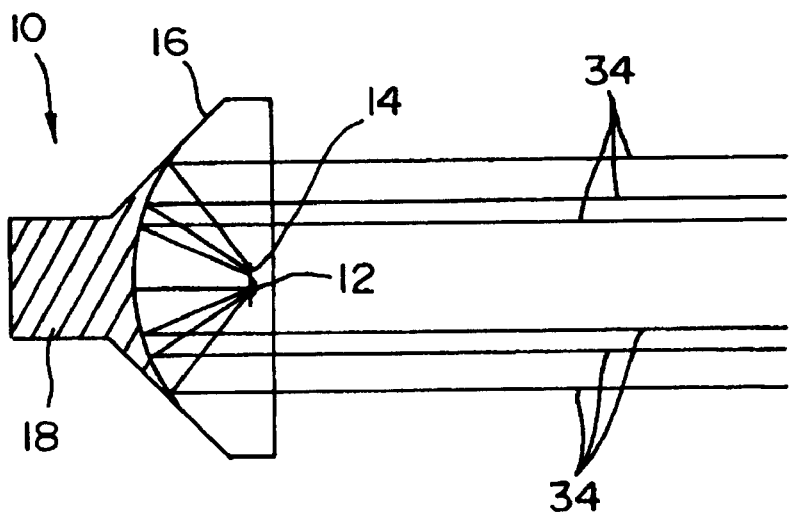
FIG. 4 is an approximation of a beam pattern of reflected energy returning to an array of receivers.

Referring, now to FIG. 4, scan head 10 is shown in cross-section. Signal reflector 16 is shown to be spherical in nature. Reflected sound waves 34 bounce off of spherical reflector 16 and are directed toward receiver array 14. In this manner the reflected sound waves are sensed without requiring any movement of the receivers or phasing between the receivers in array 14. Each receiver in array 14 senses an echo from a different point on the object being scanned providing raw data that is then converted into a three dimensional image. This simple solution to a difficult problem was an unexpected result of simple experimentation.

A spherical shaped signal reflector has a limitation in that it has a fairly deep field of focus and is not suitable for imaging vascular structures that lie just under a patient's skin down to about five (5) centimeters below the skin's surface. This problem is addressed in a another embodiment discussed below.

Figure 5:
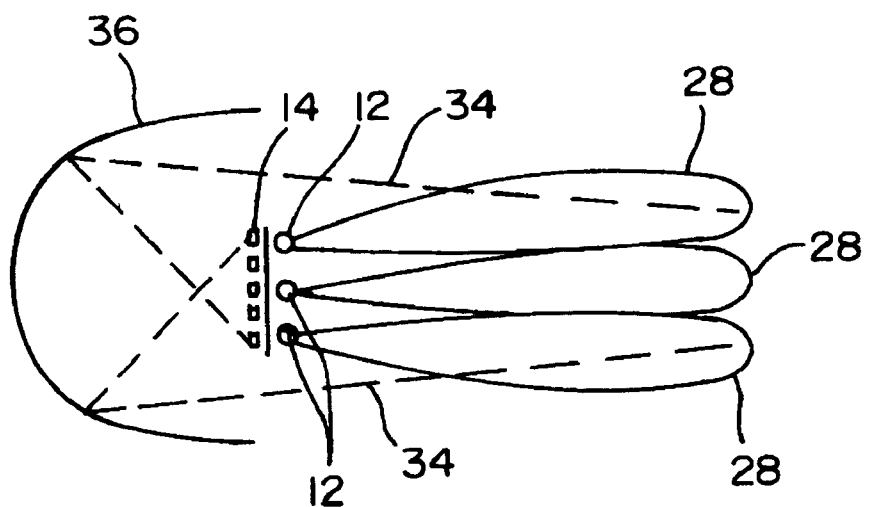
FIG. 5 is a schematic of a curved reflector with an array of transmitters and an array of receivers.

Referring now to FIG. 5, an ellipsoidal reflector 36 is shown in schematic cross-section. This embodiment encompasses the same components as described above except for the shape of reflector 16, 36. Ellipsoidal reflector 36 has two focus points. If one focii is located at the structure being imaged the ellipsoidal reflector will focus the sound energy at the other focii. For sources on axis the beam width can be very small and still give good lateral resolution. Since a large number of side lobes are created reflector 36 must be shaded to reduce this effect.

One method is to utilize bi-static mode operation as with spherical reflector 16. As shown in FIG. 5, an array of transmitters 12 are fired sequentially providing a wider field of view. The dashed lines indicate reflected sound energy that is reflected and focused by ellipsoidal reflector 36 onto an array of receivers 14. One way to reduce the side lobe problem described above would be to use a mono-static mode where each transducer acts as both a transmitter and a receiver. The location of the planar array is made to coincide with one of the focal planes at the center of the array. In the transmit mode each transducer focuses energy at a particular region in the other focal plane. The structure being imaged will reflect part of the energy and ellipsoidal reflector 36 will focus this energy onto different transducers in planar array 14 depending on the object being imaged. A receive beam pattern 34 will be similar to the transmit beam pattern 28. The response of the system will be the product of these two beam patterns.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the legitimate and valid scope of the appended claims, appropriately interpreted in accordance with the doctrine of equivalents.

What is claimed is:

1. A hand-held ultrasound device for obtaining images of features within a human body comprising:

a signal reflector, a transmitter, and a receiver, said transmitter and receiver supported by a suitable means at a focal point of said signal reflector, said transmitter emitting sound waves directed toward features being imaged, said signal reflector redirecting at least one reflected sound wave and focusing said reflected sound wave toward said receiver, said receiver sensing said reflected sound wave thereby generating a raw data signal;

a signal amplifier, a scan converter, and an image display all packaged within an enclosure and appropriately electrically connected, said signal amplifier boosting the signal strength of said raw data signal and passing boosted raw data to said scan converter, said scan converter translating said boosted raw data into an image signal and passing image signal to said image display for visual display thereon; and a source of electrical power to operate said transmitter, said receiving transducer, said signal amplifier, said scan converter and said image display.

2. A device according to claim 1, wherein said signal reflector is spherical in shape, said spherical shape having a pre-selected radii according to the desired depth of focus with signal generation and reflected signal upon said receiver located on focal plane of said signal reflector.

3. A device according to claim 1, wherein said receiver is a plurality of receivers arranged in a planar array positioned at the focal point of said reflector.

4. A device according to claim 1, wherein said signal reflector is ellipsoidal in shape therefore having two focal points, a transducer array located at one of said focal points adapted to act both as transmitter and receiver, whereby in the transmit mode the reflector creates a number of beams, equal to the number of elements in the array, that is projected in different directions, and refocuses the reflected signal onto said array of transducers to form image signals.

5. A device according to claim 1, wherein said reflector is ellipsoidal in shape and said transmitter comprises a plurality of transmitters directed toward an object to be imaged; and said receiver comprises a plurality of receivers adapted for receiving reflected signals from said reflector.

6. A device according to claim 1, wherein said signal reflector is spherical in shape, a transducer array located at said focal point and adapted to act both as transmitter and receiver, whereby in the transmit mode the reflector creates a number of beams, equal to the number of elements in the array, that are projected in different directions, and refocuses the reflected signal onto said array of transducers to form image signals.

7. A device according to claim 1, wherein said reflector is spherical in shape and said transmitter comprises a plurality of transmitters directed toward an object to be imaged, and said receiver comprises a plurality of receivers adapted for receiving reflected signals from said reflector.

* * * * *